United States Patent
Murakoshi

(10) Patent No.: US 7,095,039 B2
(45) Date of Patent: Aug. 22, 2006

(54) RADIATION IMAGE READ-OUT METHOD AND APPARATUS

(75) Inventor: Dai Murakoshi, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 156 days.

(21) Appl. No.: 10/673,400

(22) Filed: Sep. 30, 2003

(65) Prior Publication Data

US 2004/0061081 A1    Apr. 1, 2004

(30) Foreign Application Priority Data

Sep. 30, 2002    (JP)    ............... 2002/287297

(51) Int. Cl.
*G01T 1/16* (2006.01)
*H04N 1/04* (2006.01)

(52) U.S. Cl. ...................... 250/591; 250/580

(58) Field of Classification Search ................ 250/591, 250/580, 581, 584, 586, 587, 339.02, 339.09
See application file for complete search history.

(56) References Cited

U.S. PATENT DOCUMENTS

| | | | |
|---|---|---|---|
| 4,816,679 A | 3/1989 | Sunagawa et al. | |
| 4,922,103 A | 5/1990 | Kawajiri et al. | |
| 5,301,107 A * | 4/1994 | Shimura | 378/51 |
| 5,602,402 A * | 2/1997 | Yasuda | 250/587 |
| 6,151,419 A | 11/2000 | Aoki | |
| 6,653,652 B1 * | 11/2003 | Yasuda | 250/584 |
| 2001/0022349 A1 | 9/2001 | Takahashi | |
| 2002/0003218 A1 | 1/2002 | Yasuda | |

FOREIGN PATENT DOCUMENTS

| | | |
|---|---|---|
| JP | 1-101540 | 4/1989 |
| JP | 02-079669 A | 3/1990 |
| JP | 10-336444 A | 12/1998 |

* cited by examiner

*Primary Examiner*—Otilia Gabor
(74) *Attorney, Agent, or Firm*—Sughrue Mion, PLLC

(57) ABSTRACT

Reference signal components obtained in an initial state from outputs of photoelectric conversion devices of a line sensor having received reference light produced by a reference light source are stored. The line sensor is caused to receive the reference light at a stage immediately before image readout is performed. Sensitivity signal components are acquired from the outputs of the photoelectric conversion devices having received the reference light at the stage immediately before the image readout is performed. The sensitivity signal components and the reference signal components are compared with each other, and sensitivity correction signal components for making a correction for variations in sensitivity among the photoelectric conversion devices are obtained. A correction of the output signal components, which are acquired from the photoelectric conversion devices during the image readout, is made with the sensitivity correction signal components.

20 Claims, 7 Drawing Sheets

RADIATION IMAGE READ-OUT METHOD AND APPARATUS

BACKGROUND OF THE INVENTION

1. Field of the Invention

This invention relates to a radiation image read-out method and apparatus, wherein a radiation image having been stored on a stimulable phosphor sheet is read out with a line sensor. This invention particularly relates to a radiation image read-out method and apparatus, wherein a correction is made for variations in sensitivity among photoelectric conversion devices of a line sensor.

2. Description of the Related Art

It has been proposed to use stimulable phosphors in radiation image recording and reproducing systems. Specifically, a radiation image of an object, such as a human body, is recorded on a stimulable phosphor sheet, which comprises a substrate and a layer of the stimulable phosphor overlaid on the substrate. Stimulating rays, such as a laser beam, are deflected and caused to scan pixels in the radiation image, which has been stored on the stimulable phosphor sheet, one after another. The stimulating rays cause the stimulable phosphor sheet to emit light in proportion to the amount of energy stored thereon during its exposure to the radiation. The light emitted successively from the pixels in the radiation image having been stored on the stimulable phosphor sheet, upon stimulation thereof, is photoelectrically detected and converted into an electric image signal by photoelectric read-out means. The stimulable phosphor sheet, from which the image signal has been detected, is then exposed to erasing light, and radiation energy remaining thereon is thereby released.

Also, a novel radiation image recording and reproducing system aiming at enhancement of a detection quantum efficiency in the formation of the radiation image, i.e., a radiation absorptivity, a light emission efficiency, an emitted light pickup efficiency, and the like, has been proposed in, for example, patent literature 1. With the proposed radiation image recording and reproducing system, the radiation absorbing functions and the energy storing functions of the conventional stimulable phosphor are separated from each other, and a phosphor having good radiation absorbing characteristics and a phosphor having good light emission response characteristics are utilized respectively for radiation absorption and radiation image storage. The phosphor having good radiation absorbing characteristics (i.e., the phosphor for radiation absorption) is caused to absorb the radiation and to emit light having wavelengths falling within an ultraviolet to visible region. Also, the phosphor having good light emission response characteristics (i.e., the phosphor for energy storage) is caused to absorb the light, which has been emitted by the phosphor having good radiation absorbing characteristics, and to store energy of the emitted light. The phosphor having good light emission response characteristics, on which the energy of the emitted light has been stored, is then exposed to light having wavelengths falling within a visible to infrared region, which light causes the phosphor having good light emission response characteristics to emit light in accordance with the stored energy. The light having thus been emitted by the phosphor having good light emission response characteristics is successively detected with photoelectric read-out means, and an image signal is thereby obtained.

The image signal, which has been obtained from the radiation image recording and reproducing systems described above, is then subjected to image processing, such as gradation processing and processing in the frequency domain, such that a visible radiation image, which has good image quality and can serve as an effective tool in, particularly, the efficient and accurate diagnosis of an illness, can be obtained. The image signal having been obtained from the image processing is utilized for reproducing a visible image for diagnosis, or the like, on film or on a high resolution cathode ray tube (CRT) display device. In cases where the stimulable phosphor sheet, from which the image signal has been detected, is then exposed to the erasing light, and energy remaining on the stimulable phosphor sheet is thereby released, the erased stimulable phosphor sheet is capable of being used again for the recording of a radiation image.

Novel radiation image read-out apparatuses for use in the radiation image recording and reproducing systems described above have been proposed in, for example, patent literatures 2, 3, and 4. In the proposed radiation image read-out apparatuses, from the point of view of keeping the emitted light detection time short, reducing the size of the apparatus, and keeping the cost low, a line light source for irradiating linear stimulating rays onto a stimulable phosphor sheet is utilized as a stimulating ray source, and a line sensor comprising a plurality of photoelectric conversion devices arrayed along the length direction of a linear area of the stimulable phosphor sheet, onto which linear area the stimulating rays are irradiated by the line light source, is utilized as photoelectric read-out means. (The length direction of the linear area of the stimulable phosphor sheet will hereinbelow be referred to as the main scanning direction.) Also, the proposed radiation image read-out apparatuses comprise scanning means for moving the stimulable phosphor sheet with respect to the line light source and the line sensor and in a direction, which is approximately normal to the length direction of the linear area of the stimulable phosphor sheet. (The direction, which is approximately normal to the length direction of the linear area of the stimulable phosphor sheet, will hereinbelow be referred to as the sub-scanning direction.)

However, the line sensor utilized in the radiation image recording and reproducing systems described above comprises the plurality of the photoelectric conversion devices, which are arrayed in the main scanning direction, and variations in light receiving sensitivity occur among the photoelectric conversion devices. Therefore, the problems occur in that an artifact due to the variations in sensitivity among the photoelectric conversion devices is mixed in an output signal obtained from the line sensor, and an image having good image quality cannot be obtained. For example, in cases where the line sensor is constituted of a charge coupled device (CCD) image sensor, photodiodes (hereinbelow referred to as PD's) of the CCD image sensor, which PD's act as the photoelectric conversion devices, are independent of one another, and the sensitivities of the PD's are not identical with one another. Therefore, in order for an image having good image quality to be obtained, it is necessary that the outputs obtained from the PD's are corrected in accordance with the variations in sensitivity among the PD's of the CCD image sensor.

By way of example, a technique for making a correction for the variations in sensitivity among the photoelectric conversion devices of the line sensor has been proposed by the applicant in patent literature 5. With the proposed technique, light coming from a reference light source is received, and output signal components obtained from the photoelectric conversion devices are normalized with a mean value. In this manner, the correction is made for variations in sensitivity among the pixel regions of the line sensor.

Patent literature 1: U.S. Pat. Laid-Open No. 20010022349
Patent literature 2: U.S. Pat. No. 4,922,103
Patent literature 3: U.S. Pat. No. 4,816,679
Patent literature 4: Japanese Unexamined Patent Publication No. 1(1989)-101540
Patent literature 5: U.S. Patent Laid-Open No. 20020003218

However, with the aforesaid technique for making a correction for the variations in sensitivity among the photoelectric conversion devices of the line sensor, wherein the output signal components obtained from the photoelectric conversion devices are merely normalized with the mean value, the problems occur in that a profile of the line-like reference light source remains as a correction residue, and the correction for the sensitivity cannot be performed sufficiently.

Also, with the aforesaid technique for making a correction for the variations in sensitivity among the photoelectric conversion devices of the line sensor, wherein the output signal components obtained from the photoelectric conversion devices are merely normalized with the mean value, the problems occur in that a correction cannot be made for a term due to deterioration of the reference light source with the passage of time. Therefore, in order for the correction to be made accurately, it is necessary to perform operations, wherein X-rays are uniformly irradiated to a stimulable phosphor sheet, and correction values are calculated from comparison with the signal obtained from the stimulable phosphor sheet having been uniformly exposed to the X-rays. However, the correction processing accompanying the uniform irradiation of the X-rays gives a stress to the user.

SUMMARY OF THE INVENTION

The primary object of the present invention is to provide a radiation image read-out method, wherein a sufficient correction for sensitivity is capable of being made with respect to photoelectric conversion devices of a line sensor, such that a stress is not given to a user.

Another object of the present invention is to provide an apparatus for carrying out the radiation image read-out method.

The present invention provides a radiation image read-out method, comprising the steps of:

i) irradiating stimulating rays, which have been produced by a line light source, linearly along a main scanning direction and onto a stimulable phosphor sheet, on which a radiation image has been stored, the stimulating rays causing the stimulable phosphor sheet to emit light in proportion to an amount of energy stored on the stimulable phosphor sheet during exposure of the stimulable phosphor sheet to radiation, ii) receiving light, which is emitted from the linear area of the stimulable phosphor sheet exposed to the linear stimulating rays, with a line sensor comprising a plurality of photoelectric conversion devices arrayed along the main scanning direction, the received light being subjected to photoelectric conversion performed by the line sensor, iii) moving the stimulable phosphor sheet with respect to the line light source and the line sensor and in a sub-scanning direction different from the main scanning direction, and iv) successively acquiring output signal components from the photoelectric conversion devices of the line sensor in accordance with the movement, whereby an operation for reading out the radiation image from the stimulable phosphor sheet is performed, wherein the improvement comprises the provision of the steps of:

a) previously storing reference signal components having been obtained in an initial state from the outputs of the photoelectric conversion devices of the line sensor, which has received reference light produced by a reference light source, b) causing the line sensor to receive the reference light, which is produced by the reference light source, at a stage immediately before the operation for reading out the radiation image from the stimulable phosphor sheet is performed, c) acquiring sensitivity signal components from the outputs of the photoelectric conversion devices of the line sensor having received the reference light, which is produced by the reference light source, at the stage immediately before the operation for reading out the radiation image from the stimulable phosphor sheet is performed, d) comparing the sensitivity signal components and the corresponding reference signal components with each other, sensitivity correction signal components for making a correction for variations in sensitivity among the photoelectric conversion devices of the line sensor being obtained from the comparison, and e) making a correction of the output signal components, which are acquired from the photoelectric conversion devices of the line sensor at the time of the operation for reading out the radiation image from the stimulable phosphor sheet, by use of the sensitivity correction signal components.

The radiation image read-out method in accordance with the present invention should preferably be modified such that the sensitivity correction signal components are subjected to low spatial frequency component removing processing, and the correction of the output signal components, which are acquired from the photoelectric conversion devices of the line sensor at the time of the operation for reading out the radiation image from the stimulable phosphor sheet, is made by use of the sensitivity correction signal components, which have been subjected to the low spatial frequency component removing processing.

The present invention also provides an apparatus for carrying out the radiation image read-out method in accordance with the present invention. Specifically, the present invention also provides a radiation image read-out apparatus, comprising:

i) a line light source for irradiating stimulating rays linearly along a main scanning direction and onto a stimulable phosphor sheet, on which a radiation image has been stored, the stimulating rays causing the stimulable phosphor sheet to emit light in proportion to an amount of energy stored on the stimulable phosphor sheet during exposure of the stimulable phosphor sheet to radiation, ii) a line sensor for receiving light, which is emitted from the linear area of the stimulable phosphor sheet exposed to the linear stimulating rays, and performing photoelectric conversion of the received light, the line sensor comprising a plurality of photoelectric conversion devices arrayed along the main scanning direction, iii) sub-scanning means for moving the stimulable phosphor sheet with respect to the line light source and the line sensor and in a sub-scanning direction different from the main scanning direction, and iv) read-out means for successively acquiring output signal components from the photoelectric conversion devices of the line sensor in accordance with the movement, and thereby performing an operation for reading out the radiation image from the stimulable phosphor sheet, wherein the improvement comprises the provision of:

a) a reference light source for projecting reference light onto the line sensor, b) sensitivity signal component acquiring means for acquiring sensitivity signal components from the outputs of the photoelectric conversion devices of the line sensor having received the reference light, which is produced by the reference light source, c) reference signal component storing means for storing the sensitivity signal components, which have been acquired in an initial state by the sensitivity signal component acquiring means, as reference signal components, d) correction signal component calculating means for comparing sensitivity signal components, which have been acquired by the sensitivity signal component acquiring means at a stage immediately before the operation for reading out the radiation image from the stimulable phosphor sheet is performed, and the corresponding reference signal components, which have been stored in the reference signal component storing means, with each other in order to obtain sensitivity correction signal components for making a correction for variations in sensitivity among the photoelectric conversion devices of the line sensor, and e) correction means for making a correction of the output signal components, which are acquired from the photoelectric conversion devices of the line sensor at the time of the operation for reading out the radiation image from the stimulable phosphor sheet, by use of the sensitivity correction signal components.

The radiation image read-out apparatus in accordance with the present invention should preferably be modified such that the sensitivity correction signal components are subjected to low spatial frequency component removing processing, and the correction means makes the correction of the output signal components, which are acquired from the photoelectric conversion devices of the line sensor at the time of the operation for reading out the radiation image from the stimulable phosphor sheet, by use of the sensitivity correction signal components, which have been subjected to the low frequency component removing processing.

The term "initial state" as used herein means the state in which the data concerning the reference signal components obtained from the outputs of the photoelectric conversion devices of the line sensor is to be altered at the time of, for example, delivery of the radiation image read-out apparatus, exchange of the reference light source, or exchange of the stimulable phosphor sheet.

In the radiation image read-out method and apparatus in accordance with the present invention, the acquisition of the sensitivity signal components is performed at the stage immediately before every operation for reading out the radiation image from the stimulable phosphor sheet, on which the radiation image has been stored, is to be performed. Since the purpose of the acquisition of the sensitivity signal components is to make the correction for the sensitivity of the photoelectric conversion devices, the acquisition of the sensitivity signal components should preferably be performed at the time as close to the image read-out operation as possible. However, in cases where adverse effects do not occur practically, the acquisition of the sensitivity signal components may be performed slightly before the image read-out operation is performed. Therefore, the term "stage immediately before an operation for reading out a radiation image from a stimulable phosphor sheet is performed" as used herein means the stage, in a strict sense, just (e.g., several seconds) before the operation for reading out the radiation image from the stimulable phosphor sheet is performed, the stage several minutes to several hours before the operation for reading out the radiation image from the stimulable phosphor sheet is performed, or the stage just before a radiation image recording operation is performed in the cases of a built-in type of radiation image recording and read-out apparatus, which is constituted such that the stimulable phosphor sheet is accommodated within the apparatus, and the processing ranging from the radiation image recording operation to the radiation image read-out operation is performed as continuous processing within a single case housing.

Also, in the radiation image read-out method and apparatus in accordance with the present invention, the output signal components, which are acquired from the photoelectric conversion devices of the line sensor, may be the outputs themselves obtained from the photoelectric conversion devices. Alternatively, the output signal components, which are acquired from the photoelectric conversion devices of the line sensor, may be the signal components corresponding to pixel signal components of an image signal. The photoelectric conversion devices and the pixel signal components need not necessarily correspond in one-to-one relation to each other. Specifically, one pixel signal component may be acquired from the outputs of a plurality of photoelectric conversion devices.

Further, in the radiation image read-out method and apparatus in accordance with the present invention, the low spatial frequency component removing processing may be unsharp masking processing, median filtering processing, or the like. Alternatively, the low frequency component removing processing any of other known processing techniques may be employed as the low spatial frequency component removing processing.

In the radiation image read-out method and apparatus in accordance with the present invention, as the line light source, a fluorescent lamp, a cold cathode fluorescent lamp, a light emitting diode (LED) array, or the like, may be employed. The line light source may be a light source having a linear shape as in the cases of the fluorescent lamp. Alternatively, the line light source may be a light source operating such that the produced stimulating rays are formed into a line light beam. For example, the line light source may be a broad area laser, or the like. The stimulating rays radiated out from the line light source may be radiated out continuously. Alternatively, the stimulating rays radiated out from the line light source may be radiated out as pulsed stimulating rays, which are radiated out intermittently. From the point of view of reducing noise, the stimulating rays should preferably be pulsed stimulating rays having a high intensity.

As will be understood from the specification, it should be noted that the term "moving a stimulable phosphor sheet with respect to a line light source and a line sensor" as used herein means movement of the stimulable phosphor sheet relative to the line light source and the line sensor, and embraces the cases wherein the stimulable phosphor sheet is moved while the line light source and the line sensor are kept stationary, the cases wherein the line light source and the line sensor are moved while the stimulable phosphor sheet is kept stationary, and the cases wherein both the stimulable phosphor sheet and the line light source and the line sensor are moved. In cases where the line light source and the line sensor are moved, they should be moved together with each other.

The sub-scanning direction should preferably be the direction approximately normal to the main scanning direction. However, the sub-scanning direction is not limited to the direction approximately normal to the main scanning direction. For example, the stimulable phosphor sheet may be moved with respect to the line light source and the line sensor along an oblique direction with respect to the direction approximately normal to the main scanning direction or along a zigzag movement direction, such that approximately the entire surface of the stimulable phosphor sheet may be uniformly exposed to the stimulating rays.

The line light source and the line sensor may be located on the same surface side of the stimulable phosphor sheet or on opposite surface sides of the stimulable phosphor sheet. In cases where the line light source and the line sensor are located on opposite surface sides of the stimulable phosphor sheet, the substrate of the stimulable phosphor sheet, or the like, should be formed from a material permeable to the emitted light, such that the emitted light may permeate to the surface side of the stimulable phosphor sheet opposite to the surface on the stimulating ray incidence side.

Also, in the radiation image read-out method and apparatus in accordance with the present invention, the stimulable phosphor sheet for storing the radiation image may be an ordinary stimulable phosphor sheet comprising a stimulable phosphor for absorbing radiation and storing energy from the radiation, i.e. the radiation image.

Further, the radiation image read-out method and apparatus in accordance with the present invention may be employed in the radiation image recording and reproducing system described below. Specifically, with the radiation image recording and reproducing system, the radiation absorbing functions and the energy storing functions of the conventional stimulable phosphor are separated from each other, and a phosphor having good radiation absorbing characteristics and a phosphor having good light emission response characteristics are utilized respectively for radiation absorption and radiation image storage. The phosphor having good radiation absorbing characteristics (i.e., a phosphor for radiation absorption) is caused to absorb the radiation and to emit light having wavelengths falling within an ultraviolet to visible region. Also, the phosphor having good light emission response characteristics (i.e., a phosphor for energy storage) is caused to absorb the light, which has been emitted by the phosphor having good radiation absorbing characteristics, and to store energy of the emitted light. The phosphor having good light emission response characteristics, on which the energy of the emitted light has been stored, is then exposed to light having wavelengths falling within a visible to infrared region, which light causes the phosphor having good light emission response characteristics to emit light in accordance with the stored energy. The light having thus been emitted by the phosphor having good light emission response characteristics is successively detected with photoelectric read-out means, and an image signal is thereby obtained. With the radiation image recording and reproducing system described above, the detection quantum efficiency in the formation of the radiation image, i.e., the radiation absorptivity, the light emission efficiency, the emitted light pickup efficiency, and the like, is capable of being enhanced as a whole. Therefore, in the radiation image read-out method and apparatus in accordance with the present invention, the stimulable phosphor sheet may contain the phosphor for energy storage described above.

The phosphor for energy storage absorbs the light having wavelengths falling within the ultraviolet to visible region, which light has been emitted by the phosphor for radiation absorption, and stores the energy of the emitted light as the image information. The light having wavelengths falling within the ultraviolet to visible region is the light emitted by the phosphor for radiation absorption when the phosphor for radiation absorption absorbs the radiation. Therefore, the image information having been stored on the phosphor for energy storage is also taken as the radiation image.

The reference light source utilized in the radiation image read-out method and apparatus in accordance with the present invention is the light source, which is independent of the line light source for the operation for reading out the radiation image from the stimulable phosphor sheet and is provided for making the correction for variations in sensitivity among the pixel regions of the line sensor. By way of example, the reference light source may be constituted of an LED and a light guide member provided with a diffusion surface. Alternatively, the reference light source may be an EL device, an LED array, a fluorescent lamp, or a light source, which produces light containing light having wavelengths identical with the wavelengths of the light emitted by the stimulable phosphor sheet.

With the radiation image read-out method in accordance with the present invention, in the initial state, the reference signal components are stored previously, the reference signal components having been obtained from the outputs of the photoelectric conversion devices of the line sensor, which has received the reference light produced by the reference light source. Also, at the stage immediately before the operation for reading out the radiation image from the stimulable phosphor sheet is performed, the line sensor is caused to receive the reference light, which is produced by the reference light source, and the sensitivity signal components are acquired from the outputs of the photoelectric conversion devices of the line sensor having received the reference light, which is produced by the reference light source. The sensitivity signal components and the corresponding reference signal components are then compared with each other, and the sensitivity correction signal components for making the correction for variations in sensitivity among the photoelectric conversion devices of the line sensor are obtained from the comparison. Further, at the time of the operation for reading out the radiation image from the stimulable phosphor sheet, the correction of the output signal components, which are acquired from the photoelectric conversion devices of the line sensor, is made by use of the sensitivity correction signal components. Therefore, with the radiation image read-out method in accordance with the present invention, uniform irradiation of the X-rays for the correction for the sensitivity need not be performed at the time of every operation for reading out the radiation image from the stimulable phosphor sheet. Also, an artifact due to variations in sensitivity among the photoelectric conversion devices of the line sensor is capable of being suppressed easily and sufficiently, and an image having good image quality is capable of being obtained.

The radiation image read-out apparatus in accordance with the present invention comprises the reference light source for projecting the reference light onto the line sensor, and the sensitivity signal component acquiring means for acquiring the sensitivity signal components from the outputs of the photoelectric conversion devices of the line sensor having received the reference light, which is produced by the reference light source. The radiation image read-out apparatus in accordance with the present invention also comprises the reference signal component storing means for storing the sensitivity signal components, which have been acquired in the initial state by the sensitivity signal component acquiring means, as the reference signal components. The radiation image read-out apparatus in accordance with the present invention further comprises the correction signal component calculating means for comparing the sensitivity signal components, which have been acquired by the sensitivity signal component acquiring means at the stage immediately before the operation for reading out the radiation image from the stimulable phosphor sheet is performed, and the corresponding reference signal components, which have been stored in the reference signal component storing means, with each other in order to obtain the sensitivity correction signal components for making the correction for variations in sensitivity among the photoelectric conversion devices of the line sensor. The radiation image read-out apparatus in accordance with the present invention still further comprises the correction means for making the correction of the output signal components, which are acquired from the photoelectric conversion devices of the line sensor at the time of the operation for reading out the radiation image from the stimulable phosphor sheet, by use of the sensitivity correction signal components. Therefore, with the radiation image read-out apparatus in accordance with the present invention, uniform irradiation of the X-rays for the correction for the sensitivity need not be performed at the time of every operation for reading out the radiation image from the stimulable phosphor sheet. Also, an artifact due to variations in sensitivity among the photoelectric conversion devices of the line sensor is capable of being suppressed easily and sufficiently, and an image having good image quality is capable of being obtained.

The radiation image read-out method and apparatus in accordance with the present invention may be modified such that the sensitivity correction signal components are subjected to the low frequency component removing processing, and the correction of the output signal components, which are acquired from the photoelectric conversion devices of the line sensor at the time of the operation for reading out the radiation image from the stimulable phosphor sheet, is made by use of the sensitivity correction signal components, which have been subjected to the low frequency component removing processing. With the modifications described above, in cases where a change occurs with the distribution of intensities of the light produced by the reference light source, adverse effects of the change in light intensity distribution are capable of being suppressed, and therefore an image having good image quality is capable of being obtained.

DESCRIPTION OF THE PREFERRED EMBODIMENTS

The present invention will hereinbelow be described in further detail with reference to the accompanying drawings.

Figure 1:
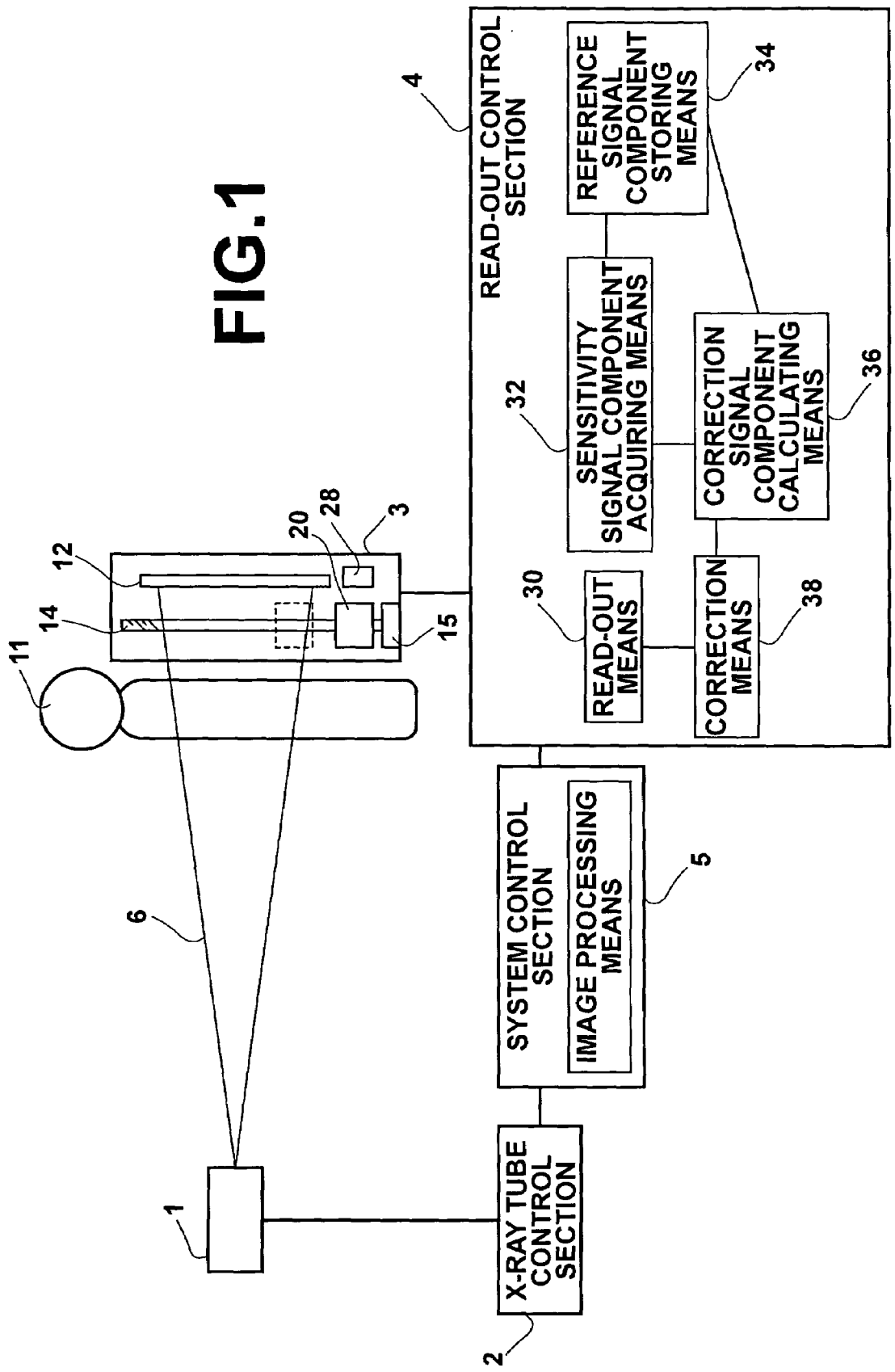
FIG. 1 is a schematic view showing a CR system provided with an embodiment of the radiation image read-out apparatus in accordance with the present invention.
Figure 2:
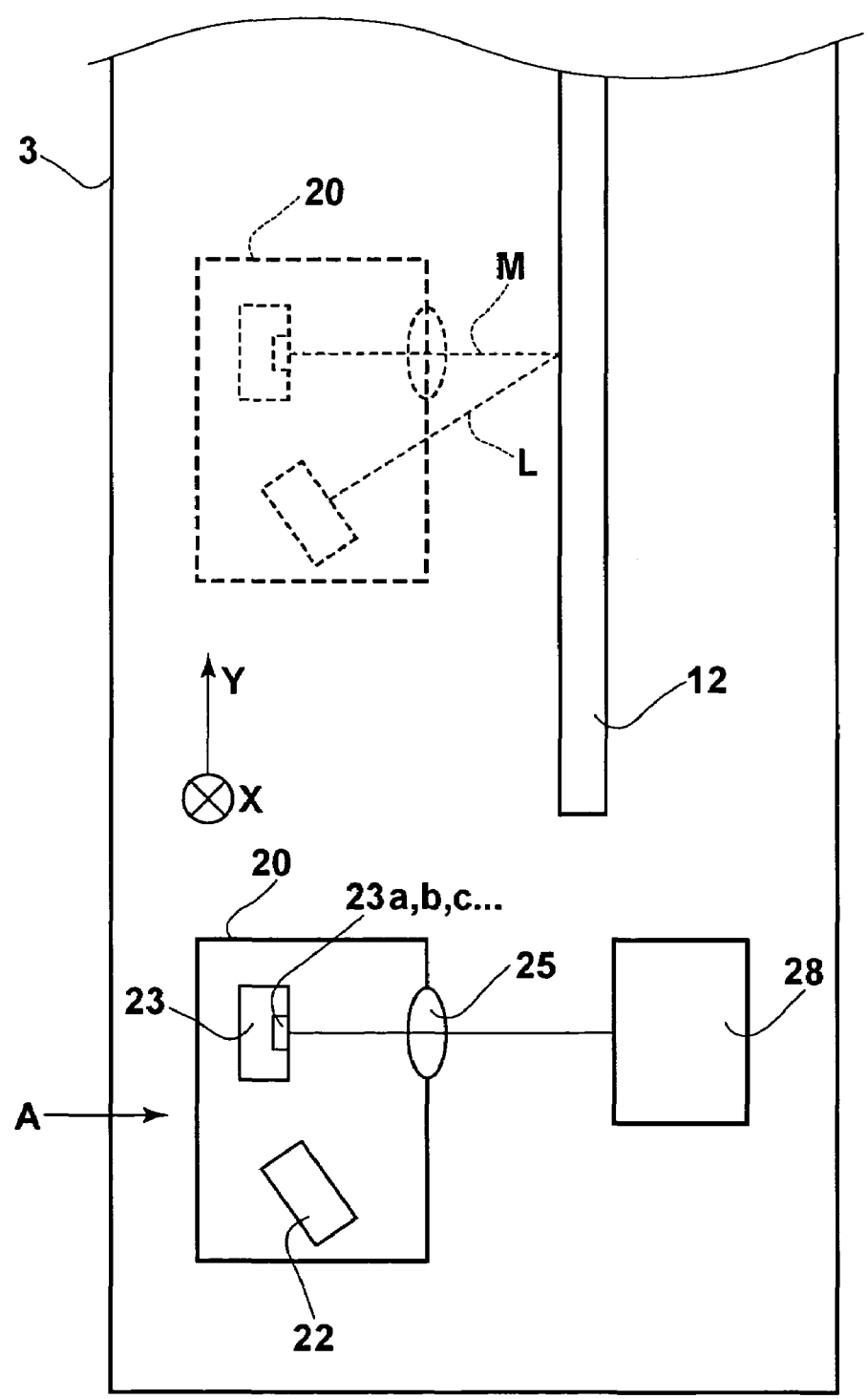
FIG. 2 is an enlarged sectional side view showing part of the radiation image read-out apparatus shown in FIG. 1.

FIG. 1 is a schematic view showing a computed radiography (CR) system provided with an embodiment of the radiation image read-out apparatus in accordance with the present invention. FIG. 2 is an enlarged sectional side view showing part of the radiation image read-out apparatus shown in FIG. 1.

As illustrated in FIG. 1, the CR system comprises a radiation image recording apparatus, a radiation image read-out apparatus, and a system control section 5. The radiation image recording apparatus comprises an X-ray source 1 for irradiating X-rays to an object 11, such as a human body, and an X-ray tube control section 2 for controlling an X-ray tube. The radiation image read-out apparatus comprises a stimulable phosphor sheet 12, which is capable of storing a radiation image thereon when being exposed to the X-rays carrying image information of the object 11. The radiation image read-out apparatus also comprises a read-out machine 3, which is provided with a scanning apparatus 20 for performing an operation for reading out the radiation image from the stimulable phosphor sheet 12, and the like. The radiation image read-out apparatus further comprises a read-out control section 4 for controlling the image read-out operation of the read-out machine 3. The system control section 5 controls the radiation image recording apparatus and the radiation image read-out apparatus and is provided with image processing means for receiving an image signal, which is obtained from the radiation image read-out apparatus, and performing image processing, and the like, on the received image signal.

As illustrated in detail in FIG. 2, the read-out machine 3 of the radiation image read-out apparatus in accordance with the present invention comprises the stimulable phosphor sheet 12, which is supported at a predetermined position, and the scanning apparatus 20. The scanner head 20 accommodates therein a line light source (linear light source) 22, a CCD line sensor 23, and a converging lens array 25 located on the side of the CCD line sensor 23, which side stands facing the stimulable phosphor sheet 12. As illustrated in FIG. 1, the read-out machine 3 also comprises sub-scanning means 15 for vertically moving the scanning apparatus 20. The read-out machine 3 further comprises a reference light source 28, which is utilized for the formation of correction signal components, and erasing light source (not shown).

The sub-scanning means 15 is provided with an internally threaded section (not shown), which is engaged with a ball screw 14 capable of being rotated, and the like. The ball screw 14 is rotated forwardly and reversely, and the scanning apparatus 20 is moved vertically by the rotation of the ball screw 14.

By way of example, the line light source 22 is constituted of a laser diode array and a cylindrical lens. The laser diode array comprises a plurality of laser diodes, which are arrayed in a line, and each of which produces a laser beam having wavelengths falling within the range of 650 nm to 690 nm and acting as stimulating rays. The stimulating rays, which have been radiated out in a divergent light state from each of the laser diodes, are converged by the cylindrical lens only in one direction into a fan beam. Stimulating rays L, which are composed of the thus obtained fan beams, are linearly irradiated to an area of the stimulable phosphor sheet 12.

The CCD line sensor 23 comprises a plurality of photoelectric conversion devices (sensor chips) 23a, 23b, 23c, . . . , which are arrayed in a line. The CCD line sensor 23 is located such that the photoelectric conversion devices 23a, 23b, 23c, . . . stand side by side along a length direction X of the linear area of the stimulable phosphor sheet 12 illustrated in FIG. 2, which linear area is exposed to the stimulating rays L, i.e. along the direction normal to the plane of the sheet of FIG. 2.

By way of example, the converging lens array 25 comprises a plurality of distributed index lenses. The converging lens array 25 is located such that the distributed index lenses stand side by side along the length direction X of the linear area of the stimulable phosphor sheet 12 illustrated in FIG. 2, which linear area is exposed to the stimulating rays L. Each of the distributed index lenses converges light M, which is emitted by the stimulable phosphor sheet 12 when the stimulable phosphor sheet 12 is exposed to the stimulating rays L, and guides the emitted light M toward the CCD line sensor 23.

A stimulating ray cut-off filter (not shown) for filtering out the stimulating rays L, which have been reflected from the stimulable phosphor sheet 12, is located between the CCD line sensor 23 and the converging lens array 25.

By way of example, the reference light source 28 is constituted of a Light Emitting Diode(LED) and an optical fiber having a light diffusing surface. Alternatively, the reference light source 28 may be constituted of a fluorescent lamp, an EL device, an illuminating device, which produces light containing light having wavelengths identical with the wavelengths of the light M emitted by the stimulable phosphor sheet 12, or the like. Also, the reference light source 28 is located at a position positively shifted from the focusing point of the converging lens array 25 of the scanning apparatus 20. In cases where the reference light source 28 is thus located at the position shifted from the focusing point of the converging lens array 25 of the scanning apparatus 20, mis-correction due to dust, which clings to the light source surface of the reference light source 28, and due to flaws in the light source surface of the reference light source 28 is capable of being suppressed. Further, in order for mis-correction due to dust clinging to the light source surface of the reference light source 28 to be suppressed even further, the reference light source 28 should preferably be provided with dust removing means for removing dust from the light source surface of the reference light source 28 by the utilization of air, a brush, electrostatic attraction, or the like.

The erasing light source (not shown) is located at, for example, a position behind a support section for supporting the stimulable phosphor sheet 12. At a stage after the image read-out operation has been performed on the stimulable phosphor sheet 12 by the radiation image read-out apparatus and before the next radiation image recording operation is performed on the stimulable phosphor sheet 12, erasing light is irradiated from the erasing light source to the stimulable phosphor sheet 12 in order to release energy remaining on the stimulable phosphor sheet 12.

The read-out control section 4 of the radiation image read-out apparatus comprises read-out means 30 for successively acquiring output signal components from the photoelectric conversion devices 23a, 23b, 23c, . . . of the CCD line sensor 23 and thereby reading out the radiation image, which has been stored on the stimulable phosphor sheet 12. The read-out control section 4 also comprises sensitivity signal component acquiring means 32 for acquiring sensitivity signal components from the outputs of the photoelectric conversion devices 23a, 23b, 23c, . . . of the CCD line sensor 23 having received reference light, which is produced by the reference light source 28. The read-out control section 4 further comprises reference signal component storing means 34 for storing the sensitivity signal components, which have been acquired in an initial state (for example, in the state at the time of delivery of the radiation image read-out apparatus, exchange of the reference light source 28, or exchange of the stimulable phosphor sheet 12) by the sensitivity signal component acquiring means 32, as reference signal components $H_r(p)$. The read-out control section 4 still further comprises correction signal component calculating means 36 for comparing sensitivity signal components $H_n(p)$, which have been acquired by the sensitivity signal component acquiring means 32 at a stage immediately before the operation for reading out the radiation image from the stimulable phosphor sheet 12 is performed, and the corresponding reference signal components $H_r(p)$, which have been stored in the reference signal component storing means 34, with each other in order to obtain sensitivity correction signal components $H_c(p)$ for making a correction of the output signal components acquired from the photoelectric conversion devices 23a, 23b, 23c, . . . of the CCD line sensor 23. The read-out control section 4 also comprises correction means 38 for making a correction of the output signal components, which are acquired from the photoelectric conversion devices 23a, 23b, 23c, . . . of the CCD line sensor 23 at the time of the operation for reading out the radiation image from the stimulable phosphor sheet 12 with the read-out means 30, by use of the sensitivity correction signal components $H_c(p)$.

The acquisition of the sensitivity signal components is performed by the sensitivity signal component acquiring means 32 in the manner described below.

Specifically, in a state in which the reference light source 28 is turned off, dark read-out signal components $H_d(p)$ are acquired from the outputs of the CCD line sensor 23. Thereafter, in a state in which the reference light source 28 is turned on, light source read-out signal components $H_o(p)$ are acquired from the outputs of the CCD line sensor 23 having received the reference light produced by the reference light source 28. The dark read-out signal components $H_d(p)$ are then subtracted from the corresponding light source read-out signal components $H_o(p)$. In this manner, signal components $H_1(p)$ are obtained from the subtraction represented by the formula $H_1(p)=H_o(p)-H_d(p)$. The thus obtained signal components $H_1(p)$ are normalized by use of a mean value $H_{1ave}$ of the signal components $H_1(p)$, and sensitivity signal components $H_2(p)$ are obtained. The sensitivity signal components $H_2(p)$ are represented by the formula $H_2(p)=H_1(p)/H_{1ave}$. In this specification, "p" represents the pixel positions lying along the main scanning direction. The pixels and the photoelectric conversion devices 23a, 23b, 23c, . . . for acquiring pixel signal components representing the pixels need not necessarily correspond in one-to-one relation to each other. Specifically, one pixel signal component may be acquired from the outputs of a plurality of photoelectric conversion devices. The dark read-out signal components $H_d(p)$, which are acquired from the outputs of the CCD line sensor 23, may be obtained by reading the outputs of the CCD line sensor

23 only one time. However, the dark read-out signal components $H_d(p)$ should preferably be obtained by reading the outputs of the CCD line sensor 23 several times and averaging the values of the outputs of the CCD line sensor 23. Also, the light source read-out signal components $H_o(p)$ which are acquired from the outputs of the CCD line sensor 23, may be obtained by reading the outputs of the CCD line sensor 23 only one time. However, the light source read-out signal components $H_o(p)$ should preferably be obtained by reading the outputs of the CCD line sensor 23 several times and averaging the values of the outputs of the CCD line sensor 23. In cases where the outputs of the CCD line sensor 23 are read several times, i.e. signal components corresponding to a plurality of lines are acquired, and signal components corresponding to one line are acquired by averaging the signal components corresponding to the plurality of the lines, sway components are capable of being removed.

How the embodiment of the radiation image read-out apparatus in accordance with the present invention operates will be described hereinbelow.

Firstly, processing performed in the initial state will be described hereinbelow.

In the initial state (for example, in the state at the time of delivery of the radiation image read-out apparatus, exchange of the stimulable phosphor sheet 12, or exchange of parts of the scanner head 20), the scanner head 20 is located at a standby position A. The standby position A is the position such that, when the reference light source 28 is turned on, the reference light produced by the reference light source 28 is received by the photoelectric conversion devices 23a, 23b, 23c, . . . of the CCD line sensor 23.

Figure 3:
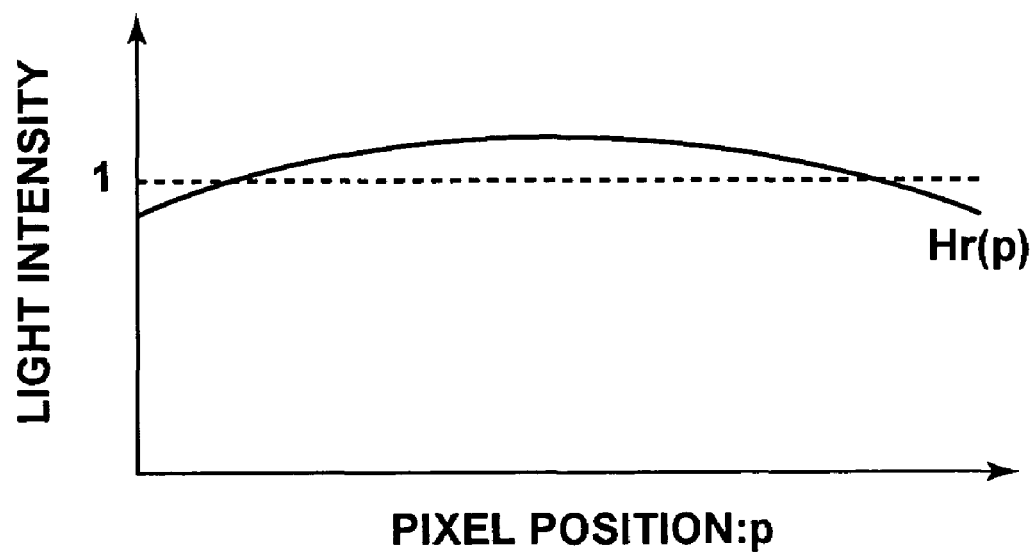
FIG. 3 is a graph showing reference signal components.

In the initial state, the sensitivity signal components $H_2(p)$ are acquired with the sensitivity signal component acquiring means 32. The sensitivity signal components $H_2(p)$ are taken as the reference signal components $H_r(p)$ to be utilized for the formation of the sensitivity correction signal components and are stored in the reference signal component storing means 34. The reference signal components $H_r(p)$ have a profile illustrated in, for example, FIG. 3. In the graph shown in FIG. 3, the light intensity is plotted on the vertical axis, and the pixel position p lying along the main scanning direction is plotted on the horizontal axis. The light intensity plotted on the vertical axis is of the normalized value obtained from normalization in which the mean value of the values of the reference signal components $H_r(p)$ is taken as 1. (Also, in each of FIG. 4, FIG. 5, FIG. 6, and FIG. 7, the light intensity plotted on the vertical axis is of the normalized value obtained from normalization in which the mean value of the values of the signal components is taken as 1.)

How a series of processing ranging from the radiation image recording operation to the radiation image read-out operation is performed in the CR system will be described hereinbelow.

Figure 4:
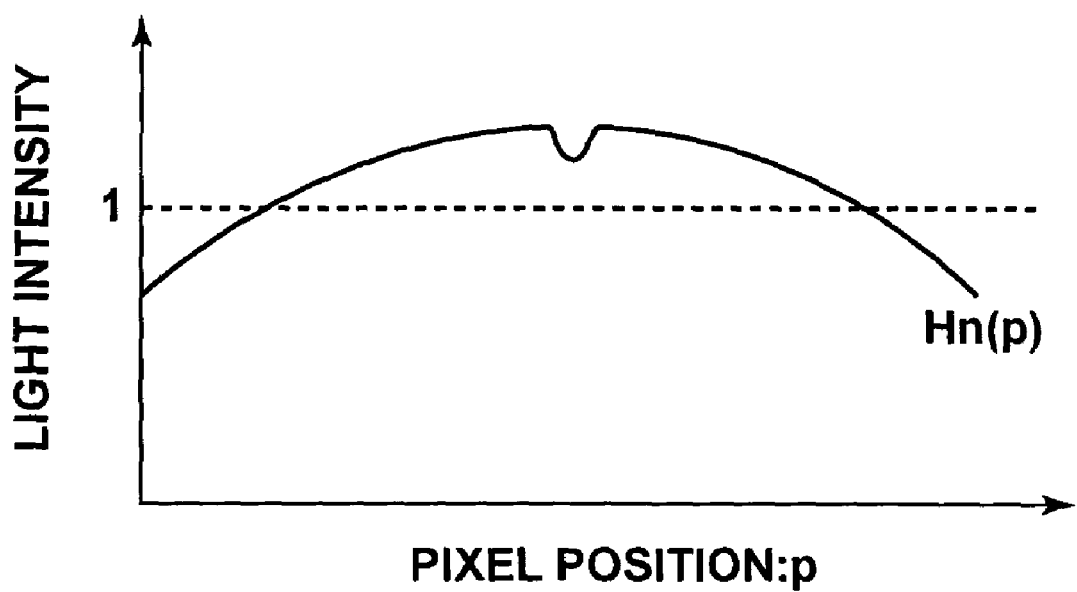
FIG. 4 is a graph showing sensitivity signal components acquired at a stage immediate before an operation for reading out a radiation image from a stimulable phosphor sheet is performed.
Figure 5:
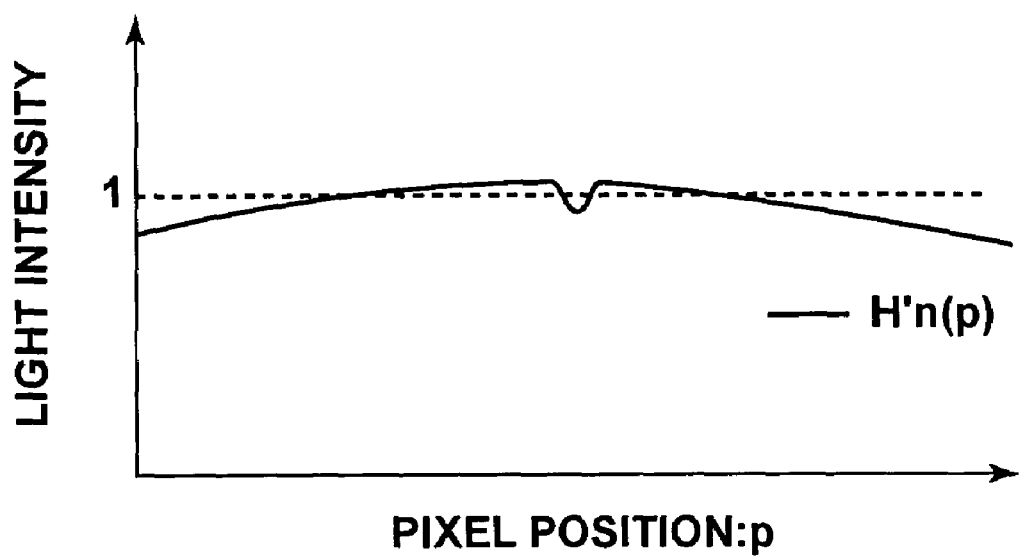
FIG. 5 is a graph showing sensitivity correction signal components.
Figure 6:
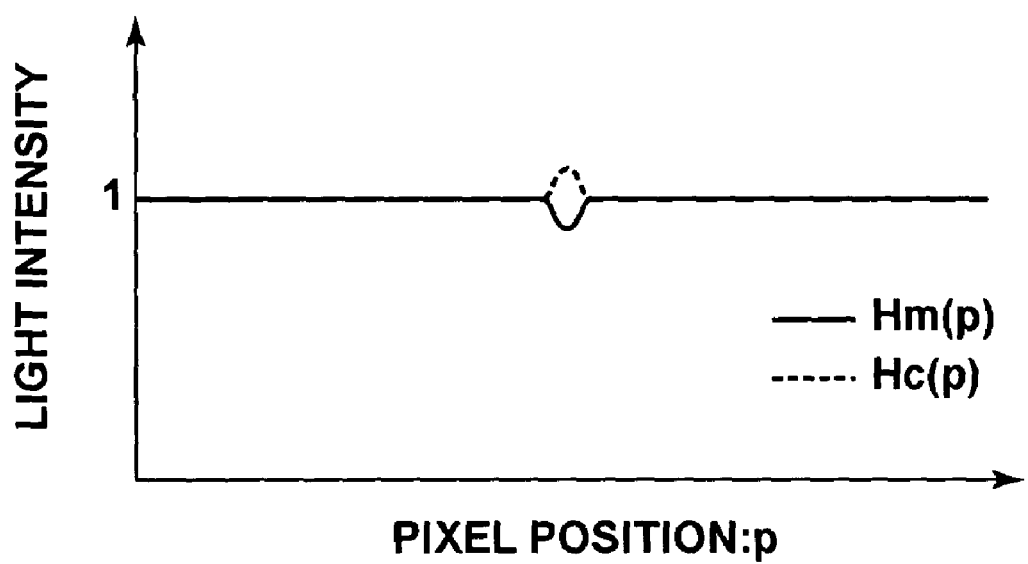
FIG. 6 is a graph showing sensitivity correction signal components having been subjected to unsharp masking processing.

Before the radiation image recording operation and the radiation image read-out operation are performed, the sensitivity correction signal components are formed. At this stage, the scanning apparatus 20 is located at the standby position A, and the sensitivity signal components $H_2(p)$ are acquired in the same manner as that in the cases of the initial state. The thus acquired sensitivity signal components $H_2(p)$ are taken as the read-out stage sensitivity signal components $H_n(p)$ immediately before the radiation image read-out operation is performed. The read-out stage sensitivity signal components $H_n(p)$ have a profile illustrated in, for example, FIG. 4. The profile of the read-out stage sensitivity signal components $H_n(p)$ illustrated in FIG. 4 is different from the profile of the reference signal components $H_r(p)$ illustrated in FIG. 3 and indicates that a change from the initial state has occurred with the reference light source 28 and/or the sensitivity, or the like, of the photoelectric conversion devices 23a, 23b, 23c, . . . of the CCD line sensor 23. Also, the profile of the read-out stage sensitivity signal components $H_n(p)$ illustrated in FIG. 4 contains a discontinuous region in the vicinity of the center point with respect to the main scanning direction.

In the correction signal component calculating means 36, the read-out stage sensitivity signal components $H_n(p)$ are divided by the corresponding reference signal components $H_r(p)$, and signal components $H_n'(p)$ are obtained from the division processing. The signal components $H_n'(p)$ are represented by the formula $H_n'(p)=H_n(p)/H_r(p)$ and have a profile illustrated in FIG. 5. By way of example, the reciprocals of the signal components $H_n'(p)$ may be taken as the sensitivity correction signal components. However, in this embodiment, unsharp masking processing is performed on the signal components $H_n'(p)$ in order to remove locality change components with respect to the reference light source 28.

In this embodiment, as the unsharp masking processing, the operation processing represented by the formula shown below is performed.

$$Hm(p) = Hn'(p) - \sum_{k=-M/2}^{+M/2} \frac{Hn'(k)}{M} + \frac{\sum Hn'(p)}{\sum p}$$

In lieu of the unsharp masking processing, median filtering processing with a mask size M may be performed on the signal components $H_n'(p)$ in order to remove the low frequency components.

Signal components $H_m(p)$ are obtained from the unsharp masking processing performed on the signal components $H_n'(p)$. Also, reciprocals of the signal components $H_m(p)$ are taken as the sensitivity correction signal components $H_c(p)$. The sensitivity correction signal components $H_c(p)$ are represented by the formula $H_c(p)=1/H_m(p)$. The signal components $H_m(p)$ and the sensitivity correction signal components $H_c(p)$ have the profiles illustrated in FIG. 6. The thus obtained sensitivity correction signal components $H_c(p)$ are stored in an internal memory of the correction signal component calculating means 36. The aforesaid discontinuous region of the read-out stage sensitivity signal components $H_n(p)$ illustrated in FIG. 4 occurs due to a sensitivity failure of a photoelectric conversion device. The sensitivity correction signal components $H_c(p)$ also contain a discontinuous region corresponding to the aforesaid discontinuous region of the read-out stage sensitivity signal components $H_n(p)$ illustrated in FIG. 4. Processing described below is performed in order to determine whether correction processing with the sensitivity correction signal components $H_c(p)$ is to be performed with respect to the discontinuous region, or the pixel corresponding to the discontinuous region is to be regarded as being a defective pixel.

Figure 7:
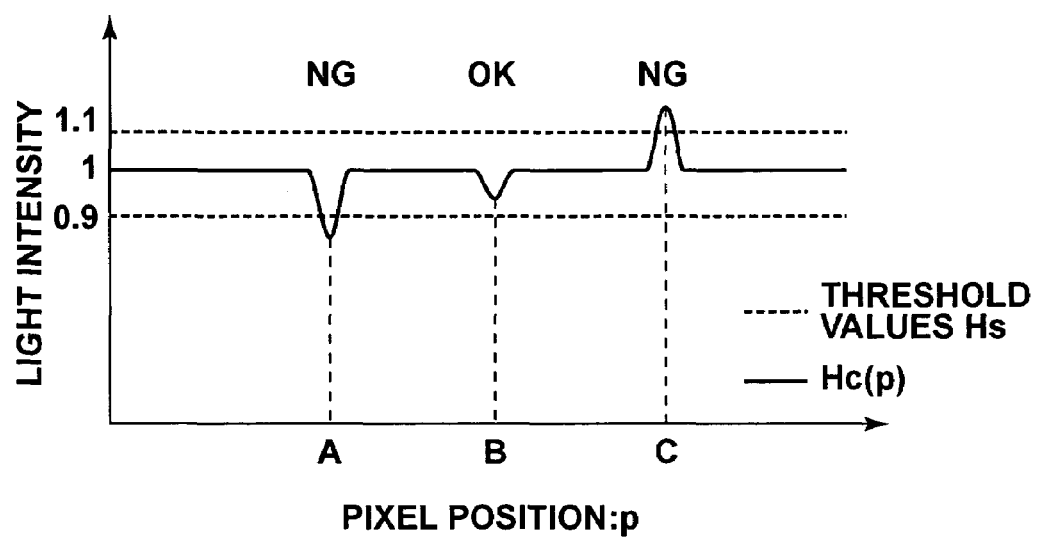
FIG. 7 is an explanatory graph showing how a defective pixel is detected.

Specifically, the correction signal component calculating means 36 performs processing for extracting a defective pixel from the sensitivity correction signal components $H_c(p)$. Threshold values Hs for making a judgment as to the defective pixel should preferably be set in accordance with a signal-to-noise ratio, which is necessary for the output obtained after a correction is made at the time of the radiation image read-out operation. However, in this embodiment, for example, values equal to the mean value of the sensitivity correction signal components $H_c(p)\pm10\%$ are taken as the threshold values Hs. For example, as illustrated in FIG. 7, values 1.1 and 0.9, which are equal to the mean value 1 of sensitivity correction signal components $H_c(p)$ ±10%, are taken respectively as the upper limit threshold value Hs and the lower limit threshold value Hs. For example, as illustrated in FIG. 7, the sensitivity correction signal components $H_c(p)$ may be discontinuous at the regions of pixels A, B, and C. In such cases, since the value of the sensitivity correction signal component $H_c$ (A) corresponding to the pixel A is smaller than the lower limit threshold value Hs, it is recognized that the pixel A is a defective pixel (NG). Also, since the value of the sensitivity correction signal component $H_c(C)$ corresponding to the pixel C is larger than the upper limit threshold value Hs, it is recognized that the pixel C is a defective pixel (NG). Therefore, it is recognized that the pixels A and C are to be subjected to a correction for defective pixels. The information representing the defective pixels A and C is stored in the internal memory of the correction signal component calculating means 36 together with the sensitivity correction signal components $H_c(p)$. As for the pixel B, since the value of the sensitivity correction signal component $H_c(B)$ corresponding to the pixel B falls within the threshold value range, it is recognized that the pixel B is not a defective pixel, and it is judged that the pixel B is to be subjected to the afore said correction with the sensitivity correction signal components $H_c(p)$. FIG. 7 shows the graph acting as an aid in facilitating the explanation of the defective pixel extracting processing and does not coincide the graphs of FIG. 3, FIG. 4, FIG. 5, and FIG. 6.

When the processing described above has been finished, a signal, which represents that the radiation image recording operation is capable of being performed, is fed from the read-out control section 4 into the system control section 5. The system control section 5 gives a notice, which indicates that the radiation image recording operation is capable of being performed, to the user.

Thereafter, the object 11 is laid at the position for image recording, and radiation 6, such as the X-rays, produced by the radiation source 1 is irradiated to the object 11. The radiation 6 carrying the image information of the object 11 is irradiated to the stimulable phosphor sheet 12, and the radiation image of the object 11 is stored on the stimulable phosphor sheet 12. At this time, the scanning apparatus 20 is located at the standby position A.

After the radiation image recording operation with the irradiation of the radiation 6 has been performed, dark correction signal components $D_d(p)$ are acquired from the CCD line sensor 23. Thereafter, the operation for reading out the radiation image from the stimulable phosphor sheet 12 is begun. Specifically, the scanner head 20 is moved at a predetermined speed and upwardly from the standby position A along the direction indicated by the arrow Y. At this time, the laser diode array of the line light source 22 is actuated, and the fan beam-like stimulating rays L are irradiated in a linear pattern, which extends along the direction X, onto the stimulable phosphor sheet 12. Also, the scanner head 20 is moved upwardly along the direction indicated by the arrow Y, which direction is normal to the direction of the linear irradiation pattern, and the scanning with the stimulating rays L in the sub-scanning direction is thus performed. As a result, the stimulable phosphor sheet 12 is scanned with the stimulating rays L in the two-dimensional directions.

When the stimulating rays L are irradiated to the stimulable phosphor sheet 12, the area of the stimulable phosphor sheet 12 exposed to the stimulating rays L emits the light M with an intensity proportional to the radiation image information stored at the exposed area. The emitted light M is converged by the converging lens array 25 onto the CCD line sensor 23 and received by the photoelectric conversion devices 23a, 23b, 23c, . . . of the CCD line sensor 23.

The photoelectric conversion devices 23a, 23b, 23c, . . . of the CCD line sensor 23 photoelectrically convert the received emitted light M and feed out output signal components D(p) in units of pixel. The read-out means 30 successively acquires the output signal components D(p) in accordance with the movement along the sub-scanning direction.

When the scanning apparatus 20 has moved to a sub-scanning end position, and the radiation image read-out operation is thus finished, the scanner head 20 is moved downwardly toward the standby position A.

Thereafter, the erasing light source (not shown) is turned on, and the erasing light produced by the erasing light source is uniformly irradiated to the entire area of the stimulable phosphor sheet 12. In this manner, energy remaining on the stimulable phosphor layer of the stimulable phosphor sheet 12 is released. Therefore, the erased stimulable phosphor sheet 12 is capable of being used again for the recording of a radiation image.

Simultaneously with the erasing processing, various corrections are made by the correction means 38. Specifically, firstly, the correction means 38 performs a dark correction by use of the dark correction signal components $D_d(p)$, which have been acquired at the stage immediately before the image read-out operation is performed. Also, the correction means 38 performs a shading correction by use of shading correction signal components, which have been acquired at the time of, for example, delivery of the radiation image read-out apparatus, exchange of the stimulable phosphor sheet 12, or exchange of parts of the scanning apparatus 20. The shading correction signal components may be one-dimensional correction signal components having been obtained along the main scanning direction. However, the shading correction signal components should preferably be two-dimensional correction signal components having been obtained along the main scanning direction and the sub-scanning direction, such that an image of good quality may be obtained with a correction for a variation in structure of the stimulable phosphor sheet 12, locality of the emitted light M, and mechanical sway along the sub-scanning direction. After the dark correction and the shading correction have been made, the correction means 38 performs the sensitivity correction processing by use of the aforesaid sensitivity correction signal components $H_c(p)$, which have been formed by the correction signal component calculating means 36.

Dark correction processed signal components $D_s(p)$ are obtained from the dark correction and the shading correction performed on the output signal components D(p), which have been acquired in units of pixel from the photoelectric conversion devices 23a, 23b, 23c, . . . of the CCD line sensor 23. In this embodiment, the dark correction processed signal components $D_s(p)$ are multiplied by the corresponding sensitivity correction signal components $H_c(p)$, and sensitivity correction processed signal components $D_c(p)$ ($=D_s(p)\cdot H_c(p)$) are obtained from the multiplication.

Further, in cases where a defective pixel has been extracted with the afore said defective pixel extracting processing, defective pixel correction processing is performed. The defective pixel correction processing may be performed with interpolation processing. The interpolation processing may be performed with one of various techniques. For example, with respect to the pixel having been recognized as being the defective pixel, the mean value of the values of two pixels adjacent to the defective pixel may be employed as the value of the defective pixel. In cases where at least two defective pixels are adjacent to each other, the values of the defective pixels may be interpolated from the values of the non-defective pixels which are adjacent to the defective pixels. Also, in cases where a plurality of defective pixels are adjacent to one another, the problems occur from the interpolating operation in that streak-like nonuniformity becomes perceptible in the obtained image. In such cases, the number of the defective pixels adjacent to one another, which number is allowable, varies in accordance with the pixel size. However, for example, in cases where the pixel size is 25 μm, and 10 defective pixels are adjacent to one another, processing for, for example, giving a warning to the user is performed. in accordance with the warning, the user is capable of conducting a countermeasure, such as exchange of the CCD line sensor 23.

The sensitivity correction processed signal components $D_c(p)$, which have been subjected to the defective pixel correction processing, are transferred into the image processing means of the system control section 5 and subjected to various kinds of image processing. The sensitivity correction processed signal components $D_c(p)$, which have been subjected to the image processing, are utilized for reproducing a visible image on an image display device, such as a CRT display device. Alternatively, the sensitivity correction processed signal components $D_c(p)$, which have been subjected to the image processing, may be utilized with an image reproducing apparatus for reproducing a visible image on film. As another alternative, the sensitivity correction processed signal components $D_c(p)$, which have been subjected to the image processing, may be stored in a storage device.

As described above, with this embodiment of the radiation image read-out apparatus in accordance with the present invention, the sensitivity correction signal components for making the correction for variations in sensitivity among the photoelectric conversion devices 23a, 23b, 23c, . . . of the CCD line sensor 23 are calculated, and the output signal components obtained from the CCD line sensor 23 are corrected by use of the sensitivity correction signal components. Therefore, the problems are capable of being prevented from occurring in that the image quality of the obtained image becomes bad due to the variations in sensitivity among the photoelectric conversion devices 23a, 23b, 23c, . . . of the CCD line sensor 23. In particular, with this embodiment of the radiation image read-out apparatus in accordance with the present invention, the sensitivity signal components acquired in the initial state are stored as the reference signal components. Also, the sensitivity signal components, which are acquired at the time of every radiation image read-out operation, are compared with the corresponding reference signal components, and the sensitivity correction signal components are thereby formed. Therefore, the correction is capable of being made for a difference in level due to the profile of the reference light source 28. Accordingly, in cases where the reference light source 28 is not an ideal line-like light source, an accurate sensitivity correction is capable of being performed. Also, in cases where the unsharp masking processing is performed, adverse effects of a change in profile of the reference light source 28 are capable of being suppressed. Further, since the defective pixel is capable of being discriminated easily, appropriate processing, such as the interpolating operation, is capable of being performed with respect to the defective pixel. Therefore, with this embodiment of the radiation image read-out apparatus in accordance with the present invention, a particular operation, such as uniform irradiation of X-rays to the stimulable phosphor sheet, which operation gives a stress to the user, need not be performed, and an image having good image quality is capable of being obtained.

In the embodiment described above, the formation of the sensitivity correction signal components is performed at the stage immediately before the radiation image recording operation is performed. Alternatively, the formation of the sensitivity correction signal components may be performed at the stage after the radiation image recording operation is performed and before the radiation image read-out operation is performed.

Also, in the embodiment described above, besides the correction for the sensitivity of the CCD line sensor 23 in accordance with the present invention, the dark correction and the shading correction are performed. However, other kinds of corrections may be performed even further. For example, a correction may be made for non-linearity of the I/O characteristics of the CCD. Also, correction processing for enhancing the signal-to-noise ratio with pixel value addition may be performed. In cases where the other kinds of corrections described above are performed, the defective pixel correction processing described above should preferably be performed at the final stage of the various kinds of the corrections.

Further, in the embodiment described above, the line light source 22 is constituted of the laser diode array. Alternatively, a line light source constituted of an LED array, or the like, may be employed.

In the radiation image read-out apparatus provided with the reference light source 28 described above, in cases where a failure occurs with the read-out image, the read-out image, which has been obtained from the operation for reading out the radiation image from the stimulable phosphor sheet 12, and a dummy image, which has been obtained from an image read-out operation performed by use of the reference light source 28, may be compared with each other. In this manner, a judgment is capable of being made as to whether the failure has occurred due to the stimulating ray source, the stimulable phosphor sheet, the light converging optical system, or the image read-out system. Therefore, the cause for the problems are capable of being found early.

Specifically, the dummy image is obtained in the manner described below. Firstly, the scanner head 20 is located at the standby position A, and the reference light source 28 is turned on. The reference light produced by the reference light source 28 is received by the CCD line sensor 23. The outputs of the CCD line sensor 23 are read a plurality of times, and signal components corresponding to a plurality of lines are acquired. The thus obtained signal components are averaged by the number of the lines, and the averaging with respect to the sub-scanning direction is thus performed. Also, the averaged signal components are normalized with the mean value with respect to the main scanning direction, and the reciprocals of the normalized signal components are stored as the shading correction signal components. Thereafter, while the scanning aparatus 20 is being located at the standby position A, the reference light source 28 is again turned on. The reference light produced by the reference light source 28 is received by the CCD line sensor 23. The outputs of the CCD line sensor 23 are read a plurality of times, and signal components corresponding to a plurality of lines are acquired. Further, a two-dimensional image is reproduced from the thus obtained signal components. The two-dimensional image is the image reflecting the shading characteristics of the light source. The signal components representing the two-dimensional image are then multiplied by the corresponding shading correction signal components, and the dummy image is thereby obtained.

The discrimination as to the cause for the failure is performed in the manner described below. Ordinarily, the dummy image obtained in the manner described above is a uniform image. However, in cases where a failure occurs with the light converging optical system or the image read-out system, the dummy image obtained in the manner described above does not represent a uniform image. Therefore, in cases where the same failure occurs with both the read-out image, which has been obtained from the operation for reading out the radiation image from the stimulable phosphor sheet 12, and the dummy image, it may be judged that a failure has occurred with the light converging optical system, the image read-out system, or the subsequent processing. In cases where the read-out image and the dummy image do not coincide with each other with respect to the failure, it may be judged that a failure has occurred with the stimulable phosphor sheet or the stimulating ray source. In order for the read-out image and the dummy image to be compared with each other, the read-out image and the dummy image may be reproduced on film and inspected visually. Alternatively, the read-out image and the dummy image may be displayed on a display screen and compared with each other.

In cases where the cause for the problems is capable of being discriminated in the manner described above, parts exchange units are capable of being set for either the stimulation system or the light converging system, and therefore the exchange cost is capable of being kept low. For example, in cases where a failure has occurred with the scanning apparatus 20, the entire scanner head need not necessarily be exchanged, and only the parts of either the light converging system or the stimulation system may be exchanged. Accordingly, the exchange cost is capable of being kept lower than the cases where the entire scanner head is exchanged.

In the aforesaid embodiment of the radiation image read-out apparatus in accordance with the present invention, the stimulable phosphor sheet for storing the radiation image may be an ordinary stimulable phosphor sheet comprising a stimulable phosphor for absorbing radiation and storing energy from the radiation, i.e. the radiation image.

Also, the aforesaid embodiment of the radiation image read-out apparatus in accordance with the present invention may be employed in the radiation image recording and reproducing system proposed in, for example, patent literature 1. With the proposed radiation image recording and reproducing system, the radiation absorbing functions and the energy storing functions of the conventional stimulable phosphor are separated from each other, and a phosphor having good radiation absorbing characteristics and a phosphor having good light emission response characteristics are utilized respectively for radiation absorption and radiation image storage. The phosphor having good radiation absorbing characteristics (i.e., a phosphor for radiation absorption) is caused to absorb the radiation and to emit light having wavelengths falling within a ultraviolet to visible region. Also, the phosphor having good light emission response characteristics (i.e., a phosphor for energy storage) is caused to absorb the light, which has been emitted by the phosphor having good radiation absorbing characteristics, and to store energy of the emitted light. The phosphor having good light emission response characteristics, on which the energy of the emitted light has been stored, is then exposed to light having wavelengths falling within a visible to infrared region, which light causes the phosphor having good light emission response characteristics to emit light in accordance with the stored energy. The light having thus been emitted by the phosphor having good light emission response characteristics is successively detected with photoelectric read-out means, and an image signal is thereby obtained. With the proposed radiation image recording and reproducing system, the detection quantum efficiency in the formation of the radiation image, i.e., the radiation absorptivity, the light emission efficiency, the emitted light pickup efficiency, and the like, is capable of being enhanced as a whole. Therefore, in the radiation image read-out apparatus in accordance with the present invention, the stimulable phosphor sheet should preferably contain the phosphor for energy storage described above. In such cases, the image quality of the obtained image is capable of being enhanced even further.

What is claimed is:

1. A radiation image read-out method, comprising the steps of:
   i) irradiating stimulating rays, which have been produced by a line light source, linearly along a main scanning direction and onto a stimulable phosphor sheet, on which a radiation image has been stored, the stimulating rays causing the stimulable phosphor sheet to emit light in proportion to an amount of energy stored on the stimulable phosphor sheet during exposure of the stimulable phosphor sheet to radiation,
   ii) receiving light, which is emitted from the linear area of the stimulable phosphor sheet exposed to the linear stimulating rays, with a line sensor comprising a plurality of photoelectric conversion devices arrayed along the main scanning direction, the received light being subjected to photoelectric conversion performed by the line sensor,
   iii) moving the stimulable phosphor sheet with respect to the line light source and the line sensor and in a sub-scanning direction different from the main scanning direction, and
   iv) successively acquiring output signal components from the photoelectric conversion devices of the line sensor in accordance with the movement, whereby an operation for reading out the radiation image from the stimulable phosphor sheet is performed, wherein the improvement comprises the provision of the steps of:
   a) previously storing reference signal components having been obtained in an initial state from the outputs of the photoelectric conversion devices of the line sensor, which has received reference light produced by a reference light source,
   b) causing the line sensor to receive the reference light, which is produced by the reference light source, at a stage immediately before the operation for reading out the radiation image from the stimulable phosphor sheet is performed,
   c) acquiring sensitivity signal components from the outputs of the photoelectric conversion devices of the line sensor having received the reference light, which is produced by the reference light source, at the stage immediately before the operation for reading out the radiation image from the stimulable phosphor sheet is performed,
   d) comparing the sensitivity signal components and the corresponding reference signal components with each other, sensitivity correction signal components for making a correction for variations in sensitivity among the photoelectric conversion devices of the line sensor being obtained from the comparison, and e) making a correction of the output signal components, which are acquired from the photoelectric conversion devices of the line sensor at the time of the operation for reading out the radiation image from the stimulable phosphor sheet, by use of the sensitivity correction signal components.

2. A method as defined in claim 1 wherein the sensitivity correction signal components are subjected to low frequency component removing processing, and the correction of the output signal components, which are acquired from the photoelectric conversion devices of the line sensor at the time of the operation for reading out the radiation image from the stimulable phosphor sheet, is made by use of the sensitivity correction signal components, which have been subjected to the low frequency component removing processing.

3. A method as defined in claim 2 wherein the stimulable phosphor sheet contains a stimulable phosphor, which is capable of absorbing light having wavelengths falling within a ultraviolet to visible region and thereby storing energy of the light having wavelengths falling within the ultraviolet to visible region, and which is capable of being stimulated by light having wavelengths falling within a visible to infrared region and thereby radiating out the stored energy as emitted light.

4. The method as defined in claim 2, wherein the low frequency component removing process is one of unsharp masking processing and median filtering processing.

5. A method as defined in claim 1 wherein the stimulable phosphor sheet contains a stimulable phosphor, which is capable of absorbing light having wavelengths falling within a ultraviolet to visible region and thereby storing energy of the light having wavelengths falling within the ultraviolet to visible region, and which is capable of being stimulated by light having wavelengths falling within a visible to infrared region and thereby radiating out the stored energy as emitted light.

6. The method as defined in claim 1, wherein the initial state is a state of the reference light source when newly installed or replaced or when the stimulable phosphor sheet is replaced.

7. The method as defined in claim 1, wherein the obtaining of the sensitivity correction signal components includes determining whether the sensitivity signal components contain a discontinuous region that represents a defective pixel on the line sensor.

8. The method as defined in claim 1, wherein the output signal components correction includes dark correction and shading correction.

9. A radiation image read-out apparatus, comprising:

i) a line light source for irradiating stimulating rays linearly along a main scanning direction and onto a stimulable phosphor sheet, on which a radiation image has been stored, the stimulating rays causing the stimulable phosphor sheet to emit light in proportion to an amount of energy stored on the stimulable phosphor sheet during exposure of the stimulable phosphor sheet to radiation, ii) a line sensor for receiving light, which is emitted from the linear area of the stimulable phosphor sheet exposed to the linear stimulating rays, and performing photoelectric conversion of the received light, the line sensor comprising a plurality of photoelectric conversion devices arrayed along the main scanning direction, iii) sub-scanning means for moving the stimulable phosphor sheet with respect to the line light source and the line sensor and in a sub-scanning direction different from the main scanning direction, and iv) read-out means for successively acquiring output signal components from the photoelectric conversion devices of the line sensor in accordance with the movement, and thereby performing an operation for reading out the radiation image from the stimulable phosphor sheet, wherein the improvement comprises the provision of:

a) a reference light source for projecting reference light onto the line sensor, b) sensitivity signal component, acquiring means for acquiring sensitivity signal components from the outputs of the photoelectric conversion devices of the line sensor having received the reference light, which is produced by the reference light source, c) reference signal component storing means for storing the sensitivity signal components, which have been acquired in an initial state by the sensitivity signal component acquiring means, as reference signal components, d) correction signal component calculating means for comparing sensitivity signal components, which have been acquired by the sensitivity signal component acquiring means at a stage immediately before the operation for reading out the radiation image from the stimulable phosphor sheet is performed, and the corresponding reference signal components, which have been stored in the reference signal component storing means, with each other in order to obtain sensitivity correction signal components for making a correction for variations in sensitivity among the photoelectric conversion devices of the line sensor, and e) correction means for making a correction of the output signal components, which are acquired from the photoelectric conversion devices of the line sensor at the time of the operation for reading out the radiation image from the stimulable phosphor sheet, by use of the sensitivity correction signal components.

10. An apparatus as defined in claim 9 wherein the sensitivity correction signal components are subjected to low spatial frequency component removing processing, and the correction means makes the correction of the output signal components, which are acquired from the photoelectric conversion devices of the line sensor at the time of the operation for reading out the radiation image from the stimulable phosphor sheet, by use of the sensitivity correction signal components, which have been subjected to the low spatial frequency component removing processing.

11. An apparatus as defined in claim 10 wherein the stimulable phosphor sheet contains a stimulable phosphor, which is capable of absorbing light having wavelengths falling within a ultraviolet to visible region and thereby storing energy of the light having wavelengths falling within the ultraviolet to visible region, and which is capable of being stimulated by light having wavelengths falling within a visible to infrared region and thereby radiating out the stored energy as emitted light.

12. The apparatus as defined in claim 6, wherein the low spatial frequency component removing process is one of unsharp masking processing and median filtering processing.

13. An apparatus as defined in claim 9 wherein the stimulable phosphor sheet contains a stimulable phosphor, which is capable of absorbing light having wavelengths falling within a ultraviolet to visible region and thereby storing energy of the light having wavelengths falling within the ultraviolet to visible region, and which is capable of being stimulated by light having wavelengths falling within a visible to infrared region and thereby radiating out the stored energy as emitted light.

14. The apparatus as defined in claim 9, wherein the initial state is a state of the reference light source when newly installed or replaced or when the stimulable phosphor sheet is replaced.

15. The apparatus as defined in claim 9, further comprising:
a dust removing device to remove dust from a surface of the reference light source.

16. The apparatus as defined in claim 15, wherein the dust removing device utilizes one of air, a brush and electrostatic attraction to remove the dust.

17. The apparatus as defined in claim 9, wherein the obtaining of the sensitivity correction signal components includes determining whether the sensitivity signal components contain a discontinuous region that represents a defective pixel on the line sensor.

18. The apparatus as defined in claim 9, wherein the output signal components correction includes dark correction and shading correction.

19. A radiation image read-out apparatus, comprising:
i) a line light source for irradiating stimulating rays linearly along a main scanning direction and onto a stimulable phosphor sheet, on which a radiation image has been stored, the stimulating rays causing the stimulable phosphor sheet to emit light in proportion to an amount of energy stored on the stimulable phosphor sheet during exposure of the stimulable phosphor sheet to radiation,
ii) a line sensor for receiving light, which is emitted from the linear area of the stimulable phosphor sheet exposed to the linear stimulating rays, and performing photoelectric conversion of the received light, the line sensor comprising a plurality of photoelectric conversion devices arrayed along the main scanning direction,
iii) sub-scanning device that moves the stimulable phosphor sheet with respect to the line light source and the line sensor and in a sub-scanning direction different from the main scanning direction, and
iv) read-out circuit that successively acquires output signal components from the photoelectric conversion devices of the line sensor in accordance with the movement, and thereby performing an operation for reading out the radiation image from the stimulable phosphor sheet, wherein the improvement comprises the provision of:
a) a reference light source for projecting reference light onto the line sensor,
b) sensitivity signal component acquiring circuit that acquires sensitivity signal components from the outputs of the photoelectric conversion devices of the line sensor having received the reference light, which is produced by the reference light source,
c) reference signal component storage that stores the sensitivity signal components, which have been acquired in an initial state by the sensitivity signal component acquiring circuit, as reference signal components,
d) correction signal component calculating circuit that compares sensitivity signal components, which have been acquired by the sensitivity signal component acquiring circuit at a stage immediately before the operation for reading out the radiation image from the stimulable phosphor sheet is performed, and the corresponding reference signal components, which have been stored in the reference signal component storage, with each other in order to obtain sensitivity correction signal components for making a correction for variations in sensitivity among the photoelectric conversion devices of the line sensor, and
e) correction circuit for making a correction of the output signal components, which are acquired from the photoelectric conversion devices of the line sensor at the time of the operation for reading out the radiation image from the stimulable phosphor sheet, by use of the sensitivity correction signal components.

20. An apparatus as defined in claim 19 wherein the sensitivity correction signal components are subjected to low spatial frequency component removing processing, and
the correction circuit makes the correction of the output signal components, which are acquired from the photoelectric conversion devices of the line sensor at the time of the operation for reading out the radiation image from the stimulable phosphor sheet, by use of the sensitivity correction signal components, which have been subjected to the low spatial frequency component removing processing.

* * * * *